United States Patent [19]
Young

[11] 4,075,505
[45] Feb. 21, 1978

[54] MOLECULAR EMISSION LAMP
[75] Inventor: Robert A. Young, Chatsworth, Calif.
[73] Assignee: Xonics, Inc., Van Nuys, Calif.
[21] Appl. No.: 757,824
[22] Filed: Jan. 10, 1977
[51] Int. Cl.² .......................................... H02M 5/04
[52] U.S. Cl. .................................... 307/88.3; 313/223; 313/227; 313/184; 313/185; 313/224; 313/15
[58] Field of Search ............. 307/88.3; 321/60, 69 R; 313/223, 224, 227, 184, 185

[56] References Cited
U.S. PATENT DOCUMENTS 2,929,922   3/1960   Schawlow et al. ............. 331/94.5 C
4,002,922   1/1977   Young ............................ 307/88.3

*Primary Examiner*—Rudolph V. Rolinec
*Assistant Examiner*—Darwin R. Hostetter
*Attorney, Agent, or Firm*—Harris, Kern, Wallen & Tinsley

[57] ABSTRACT

A method and apparatus for producing molecular radiation of a single selected gas by generating resonance photons characteristic of the single gas and at a first frequency, and directing the resonance photons into a container of the single gas producing excited molecules of the gas which molecules emit radiation at frequencies lower than the first frequency.

33 Claims, 1 Drawing Figure

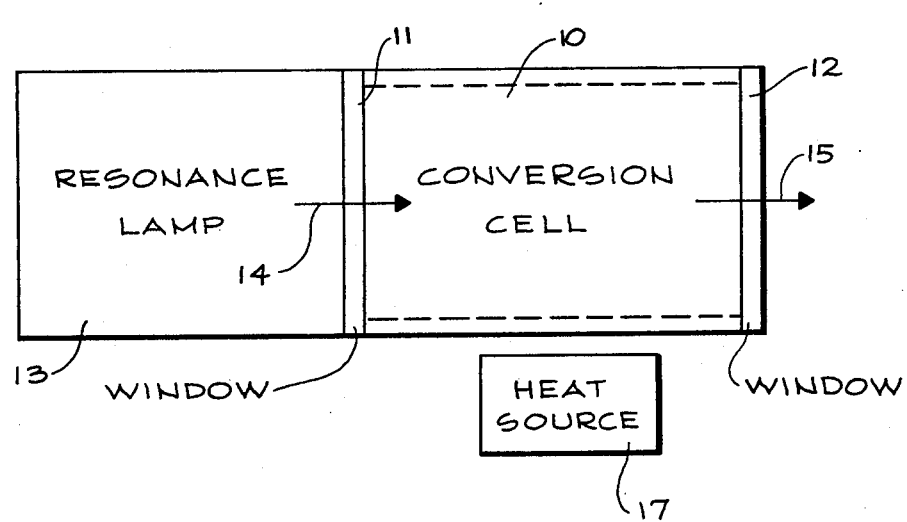

MOLECULAR EMISSION LAMP

BACKGROUND OF THE INVENTION

This invention relates generally to radiation conversion methods and apparatus, and more specifically to method and apparatus for converting a resonance photon of a single gas to a photon of a molecule of a single gas which molecule is excited, for obtaining emission of radiation from the excited molecule.

Molecular radiation sources have been used as background sources for the measurement of absorption spectra of other species, particularly in the vacuum ultraviolet. Examples of such sources are given in applicant's copending application Ser. No. 586,273, filed June 12, 1975 now U.S. Pat. No. 4,002,922. In that application, resonance photons were directed into a mixture of two gases, with the photons being characteristic of one of the gases of the mixture. It has now been found that the desired radiation can be obtained by utilizing a single gas rather than a mixture of gases, with the resonance photons producing excited molecules of the single gas which then provide the desired emission.

Accordingly, it is an object of the present invention to provide a new and improved method and apparatus for converting resonance radiation into radiation characteristic of an excited molecule while using only a single gas in the conversion cell.

A further object is to provide such a method and apparatus which can utilize a variety of gases to obtain radiation at various frequency ranges for various types of analysis.

Other objects, advantages, features and results will more fully appear in the course of the following description.

SUMMARY OF THE INVENTION

In the method of producing molecular radiation of a single selected gas, resonance photons characteristic of the single gas are generated at a first frequency and directed into a container of the single gas producing excited molecules of the single gas, with the molecules emitting radiation at frequencies lower than the first frequency.

In the apparatus for converting a resonance photon of a single gas to a photon of a molecule of the single gas, a conversion cell is charged with the single gas and a lamp is positioned for directing the resonance radiation at a first frequency characteristic of the single gas into the cell to excite the single gas producing excited molecules which emit radiation at frequencies lower than the first frequency.

The method and apparatus may utilize various types of gases, such as the rare gases which are atomic, molecular gases including gases which disassociate into atoms on treatment as by heating or otherwise, and substances which are solid at room temperature and which may be vaporized into a gaseous state by heating or the like.

BRIEF DESCRIPTION OF THE DRAWING

The single FIGURE of the drawing illustrates a lamp incorporating the presently preferred embodiment of the invention.

DESCRIPTION OF THE PREFERRED EMBODIMENTS

The device illustrated in the drawing includes a conversion cell 10 which may be cylindrical in shape with a glass wall and having windows 11, 12 at opposite ends. The windows are made of a material to pass the radiation being utilized and typically may be magnesium fluoride.

A lamp 13 is positioned for directing radiation into the cell and typically may be mounted at the window 11. The cell is charged with a single gas and the lamp generates resonance photons characteristic of the single gas and at a first frequency.

A resonance lamp is preferred as the source of the resonance photon and typical lamps are described in U.S. Pat. Nos. 3,851,214 and 3,904,907. The significant requirement for the lamp or radiation source is that it produce resonance photons which are characteristic of the single gas within the cell. A heat source 17 may be provided for heating the conversion cell in certain embodiments, to be discussed hereinbelow.

In operation, resonance photons are directed from the lamp 13 to the cell 10, as indicated by the arrow 14. In the cell, the photons produce excited atoms which in turn produce excited molecules. The excited molecules emit radiation at frequencies lower than the first frequency, usually providing a continuum spectra, with the radiation exiting through the window 12, as indicated by the arrow 15.

The rare gases such as helium, argon, krypton and xenon, are especially suitable for use with the present invention. By way of example, the lamp 13 may produce krypton resonance radiation which occurs at 1236A. When the 1236A emission is projected into the cell containing krypton, the processes of 1, 2, 3 and 4 occur.

$$Kr + photon \rightarrow Kr^* \qquad 1$$

$$Kr^* + Kr + Kr \rightarrow Kr_2^* + Kr \qquad 2$$

$$Kr^* + Kr \rightarrow Kr^{**} + Kr \qquad 3$$

$$Kr^{} + Kr + Kr \rightarrow Kr_2^{} + Kr \qquad 4$$

In the initial step in item 1, a krypton atom is converted to an excited krypton atom by absorption of a 1236A photon. The single asterisk indicates one electronic excited state and the double asterisk indicates another electronic excited state. The excited krypton atom then reacts with other krypton atoms as shown in items 2 and 3, producing the excited krypton molecule and the krypton atom in the second excited state. The krypton atom in the second excited state reacts with krypton atoms to form a krypton molecule in the second excited state, as shown in item 4. The excited krypton molecules emit at frequencies lower than the frequency of the photon, providing a continuum emission and decompose into atoms. A similar process occurs with other gases.

The other rare gases are also atomic and may be treated in the same manner as krypton. Some gases are molecular normally but may be disassociated into atoms and are equally suitable for use with the process and device of the present invention. By way of example, the cell may be charged with molecular hydrogen, which is heated by the heat source 17 to produce atomic hydrogen. The lamp 13 provides resonance photons characteristic of atomic hydrogen which react with the hydrogen atoms producing excited hydrogen molecules which in turn provide the desired emission. The same procedure may be utilized with the halogen gases.

The same procedure may also be utilized with metal halides. By way of example, a crystal of silver chloride may be placed in the cell 10 and the cell evacuated. The crystal is then heated and vaporized to provide a silver chloride gas. The lamp is selected to provide photons characteristic of atomic chlorine, producing excited chlorine molecules in the conversion cell.

If the cell is charged with a molecular gas and it absorbs a photon thus becoming excited, the molecule can radiate a multiplicity of photons of lower frequency. For example if CO is exposed to radiation 1216A characteristic of the Deuterium atom (Deuterium Lyman alpha radiation) the CO is excited to a high vibrational level of an excited electronic state from which it can, and does, radiate a multiplicity of photons to a multiplicity of lower molecular levels. In addition other states of CO are excited by collisional energy transfer and also radiate a multiplicity of wavelengths. The same procedure may be utilized with the halogen gases. Also the same procedure may be used with tiratomic molecules. For example, $CO_2$, $SO_2$ and $H_2S$.

The pressure in the cell preferably is maintained in the range of 100 torr to 10,000 torr.

Although exemplary embodiments of the invention have been disclosed and discussed, it will be understood that other applications of the invention are possible and that the embodiments disclosed may be subjected to various changes, modifications and substitutions without necessarily departing from the spirit of the invention.

I claim:

1. A method of producing molecular radiation of a single selected gas, including the steps of:
   generating resonance photons characteristic of a single gas and at a first frequency; and
   directing said resonance photons into a container of the single gas producing excited molecules of said single gas, with said molecules emitting incoherent radiation at frequencies lower than said first frequency.

2. The method of claim 1 wherein said single gas is helium.

3. The method of claim 1 wherein said single gas is argon.

4. The method of claim 1 wherein said single gas is krypton.

5. The method of claim 1 wherein said single gas is xenon.

6. The method of claim 1 wherein said single gas is a diatomic molecule.

7. The method of claim 6 wherein said single gas is CO.

8. The method of claim 1 wherein said single gas is a triatomic molecule.

9. The method of claim 8 wherein said single gas is $CO_2$.

10. The method of claim 1 wherein said single gas is a molecule which disassociates into atoms, and including the step of disassociating molecules of said single gas into atoms.

11. The method of claim 1 wherein said single gas is hydrogen, and including the step of heating molecular hydrogen to produce atomic hydrogen.

12. The method of claim 1 wherein said single gas is a halogen, and including the step of disassociating molecules of said halogen gas into atoms.

13. The method of claim 1 wherein said single gas is a metal halide, and including the step of vaporizing said metal halide into a gaseous state.

14. The method of claim 13 including disassociating said single metal halide gas.

15. The method of claim 1 including producing molecules with two different electronic states.

16. The method of claim 1 including maintaining said single gas in said container of a pressure between 100 and 10,000 torr.

17. A device for converting a resonance photon of a single gas to a photon of a molecule of the single gas, including in combination:
   a conversion cell charged with the single gas; and
   a lamp providing resonance radiation at a first frequency characteristic of said single gas;
   with said lamp positioned for directing said resonance radiation into said cell to excite said single gas in said cell producing excited molecules of said single gas, which molecules emit incoherent radiation at frequencies lower than said first frequency.

18. The device as defined in claim 17 wherein said gas is helium.

19. The device as defined in claim 17 wherein said gas is argon.

20. The device as defined in claim 17 wherein said gas is krypton.

21. The device as defined in claim 17 wherein said gas is xenon.

22. The device as defined in claim 17 wherein said gas is a diatomic molecule.

23. The device as defined in claim 17 wherein said gas is CO.

24. The device as defined in claim 17 wherein said gas is a triatomic molecule.

25. The device as defined in claim 17 wherein said gas is $CO_2$.

26. The device as defined in claim 17 wherein said single gas is a molecule which disassociates into atoms, and including means for disassociating molecules of said single gas into atoms.

27. The device as defined in claim 17 wherein said single gas is hydrogen, and including means for heating said hydrogen in said conversion cell.

28. The device as defined in claim 17 wherein said single gas is a halogen, and including means for disassociating molecules of said halogen into atoms.

29. The device as defined in claim 17 wherein said single gas is a metal halide, and including means for vaporizing said metal halide to a gaseous state.

30. The device as defined in claim 29 including means for disassociating said metal halide gas.

31. The device as defined in claim 17 wherein said single gas in said conversion cell has a pressure between 100 and 10,000 torr.

32. A method of producing molecular radiation of a single selected atomic gas, including the steps of:
   generating atomic resonance photons characteristic of a single gas and at a first frequency; and
   directing said resonance photons into a container of the single gas exciting atoms of said single gas and producing excited molecules of said single gas, with said molecules emitting incoherent radiation at frequencies lower than said first frequency.

33. A device for converting a resonance photon of a single atomic gas to a photon of a molecule of the single gas, including in combination:
   a conversion cell charged with the single atomic gas; and
   a lamp providing atomic resonance radiation at a first frequency characteristic of said single gas;
   with said lamp positioned for directing said resonance radiation into said cell to excite atoms of said single gas in said cell producing excited molecules of said single gas, which molecules emit incoherent radiation at frequencies lower than said first frequency.

* * * * *